United States Patent [19]
Luo

[11] Patent Number: 5,998,166
[45] Date of Patent: Dec. 7, 1999

[54] CD16-II VARIANTS

[75] Inventor: Shun Luo, Needham, Mass.

[73] Assignee: Applied Research Systems ARS Holding N.V., Curacao, Netherlands

[21] Appl. No.: 08/667,939

[22] Filed: Jun. 24, 1996

Related U.S. Application Data

[62] Division of application No. 08/433,123, May 3, 1995.

[51] Int. Cl.$^6$ .................................................. C12N 15/00
[52] U.S. Cl. .......................... 435/69.1; 536/23.5; 530/350
[58] Field of Search .......................... 536/23.5; 530/350, 530/387.1; 435/69.1

[56] References Cited

FOREIGN PATENT DOCUMENTS 0343950 11/1989 European Pat. Off. .
614978 9/1994 European Pat. Off. ........ C12N 15/12

OTHER PUBLICATIONS

Gary A. Peltz et al. "Human EcyRIII: Cloning, expression, and identification of the chromosomal locus of two Fc receptors for IgG", Proc. Natl. Acad.Sci.USA, vol. 86, pp. 1013–1017 (1989).

David Simmons et al. "The Fcy receptor of natural killer cells is a phospholipid–linked membrane protein", Nature vol.333, 568–570 Jun. 9, 1988.

Richard G. Hoover et al. "Autoregulatory Circuits in Myeloma", The American Society for Clinical Investigation, Inc. vol.95, Jan. 1995, pp. 241–247.

Christophe Teillaud et al. "Soluble CD16 Binds Peripheral Blood Mononuclear Cells and Inhibits Pokeweed–Mitogen–Induced Responses", Blood, vol.82, No. 10 Nov 15, 1993:pp. 3081–3090.

R. G. M. Bredius et al. Role of neutrophil FcyRIIa (CD32) and FcyRIIIb (CD16) polymorphic forms in phagoctosis of human IgG1–and IgG3–opsonized bacteria and erythrocytes immunology 1994 83 624–630.

Tom W. J. Huizinga et al. "Material Genomic Neutrophil FcRIII Deficiency Leading to Neonatal Isoimune Neutropeina", Blood, vol. 76, No. 10 Nov. 15, 1990 pp.1927–1932.

Lewis L. Lanier et al. "Membrane Anchoring of a Human IgG Fc Receptor (CD16) Determined by a Single Amino Acid", Science, vol. 246 pp.1611–1613 Dec. 22, 1989.

Bernard Scallon et al. "A human imuniglobulin G receptor exists in both polypeptide–anchored and phosphatidylinositol–glycan–anchored forms", Immunology, vol. 86, pp. 5079–5083, Jul. 1989.

Jeffrey Ravetch et al. "Alternative Membrane Forms of FcyRIII(CD16) On Human Natural Killer Cells and Neutrophils", J. Exp. Med, vol.170: 481–497.

Howard Fleit et al. "A Soluble Form of FcyRIII is Present in Human Serum and Other Body Fluids and is Elevated at Sites of Inflammation", Blood, vol. 79 No. 10 May 15, 1992, pp. 2721–2728.

C. Mathiot et al. "Correlation Between Soluble Serum CD16 (sCD16) Levels and Disease Stage in Patients with Multiple Myeloma", Journal of Clinical Immunology, vol.13 No. 1, 1993 pp. 41–48.

Jan G.J. van de Winkel et al. "Human IgG Fc receptor heterogeneity: molecular aspects and clinical implications", Immunology Today, vol. 14 No. 5 1993 pp. 215–221.

Capel et al., "Heterogeneity of Human IgF Fc Receptors, " Immunomethods, vol. 4, No. 1, pp. 25–34, 1994.

Luo, S., "Reverse Transcription–based Polymerase Chain Reaction Cloning of Fc–gamma–R–III Type II variants: Indicating a Polymorphism of Human CD16–II, " Blood, vol. 86, No. 10 (suppl. 1), Dec. 1–5 1995.

Trounstine et al, International Immunology, 2:303–310 1990.

Farber et al, "Rat CD16 is Defined by a Family of Class III Fcgamma Receptors Requiring Co–Expression of Heteroprotein Subunits"; J. of Immun., 146(12); 4352–4361 (1991).

Hass et al, "Identification of a New Genetic IgG–Fc Receptor Polylymorphism Present of NK Cell and Macrophage FcgammaRIIIA"; BloodB4:184a (1994).

Huizinga et al, "Soluble Fcgamma Receptor III in Human Plasma Originates from Release by Neutrophils"; J. Clin. Invest., 86:416–423 (1990).

Ory, et al, "Characterization of Polymorphic Forms of Fc Receptor III on Human Neutrophils"; J. Clin. Invest., 83:1676–1681 (1989).

Rieger et al., Glossary of Genetics and Cytogenetics, page 17, 1976.

Ayala et al., Modern Genetics, page 45, 1980.

Lazar et al., Molecular and Cellular Biology 8:1247–52, Mar. 1988.

Scallon et al. PNAS 86:5079–83, 1989.

*Primary Examiner*—Paula K. Hutzell
*Assistant Examiner*—Elaine Lazar-Wesley
*Attorney, Agent, or Firm*—Browdy and Neimark

[57] ABSTRACT

Human CD16-II variants, DNA sequences coding for them, their use in therapy and/or in diagnosis of autoimmune diseases and inflammatory illnesses, as well as pharmaceutical compositions comprising them, are disclosed. The sequence listing for the new polypeptides is provided.

8 Claims, 7 Drawing Sheets

FIG. 1A

```
CD16I_1      MWQLLLPTALLLLVSAGMRTEDLPKAVVFLEPQWYSVLEK    40
CD16I_4      MWQLLLPTALLLLVSAGMRTEDLPKAVVFLEPQWYSVLEK    40
CD16I_3      MWQLLLPTALLLLVSAGMRTEDLPKAVVFLEPQWYSVLEK    40
CD16I_2      MWQLLLPTALLLLVSAGMRTEDLPKAVVFLEPQWYRVLEK    40
FCG3_HUMAN   MWQLLLPTALLLLVSAGMRTEDLPKAVVFLEPQWYRVLEK    40
CD16II_1     MWQLLLPTALLLLVSAGMRTEDLPKAVVFLEPQWYRVLEK    40
CD16II_4     MWQLLLPTALLLLVSAGMRTEDLPKAVVFLEPQWYRVLEK    40
CD16II_2     MWQLLLPTALLLLVSAGMRTEDLPKAVVFLEPQWYSVLEK    40
CD16II_3     MWQLLLPTALLLLVSAGMRTEDLPKAVVFLEPQWYRVLEK    40
             ***************************************.***

CD16I_1      DSVTLKCQGAYSPEDNSTQWFHNESLISSQASSYFIDAAT    80
CD16I_4      DSVTLKCQGAYSPEDNSTQWFHNESLISSQASSYFIDAAT    80
CD16I_3      DSVTLKCQGAYSPEDNSTQWFHNESLISSQASSYFIDAAT    80
CD16I_2      DSVTLKCQGAYSPEDNSTQWFHNENLISSQASSYFIDAAT    80
FCG3_HUMAN   DSVTLKCQGAYSPEDNSTQWFHNESLISSQASSYFIDAAT    80
CD16II_1     DSVTLKCQGAYSPEDNSTQWFHNESLISSQASSYFIDAAT    80
CD16II_4     DSVTLKCQGAYSPEDNSTQWFHNESLISSQASSYFIDAAT    80
CD16II_2     DSVTLKCQGAYSPEDNSTQWFHKENLISSQASSYFIDAAT    80
CD16II_3     DSVTLKCQGAYSPEDNSTQWFHKENLISSQASSYFIDAAT    80
             **********************.*.***************

CD16I_1      VNDSGEYRCQTNLSTLSDPVQLEVHIGWLLLQAPRWVFKE   120
CD16I_4      VDDSGEYRCQTNLSTLSDPVQLEVHIGWLLLQAPRWVFKE   120
CD16I_3      VNDSGEYRCQTNLSTLSDPVQLEVHIGWLLLQAPRWVFKE   120
CD16I_2      VDDSGEYRCQTNLSTLSDPVQLEVHVGWLLLQAPRWVFKE   120
FCG3_HUMAN   VDDSGEYRCQTNLSTLSDPVQLEVHIGWLLLQAPRWVFKE   120
CD16II_1     VDDSGEYRCQTNLSTLSDPVQLEVHIGWLLLQAPRWVFKE   120
CD16II_4     VDDSGEYRCQTNLSTLSDPVQLEVHIGWLLLQAPRWVFKE   120
CD16II_2     VDDSGEYRCQTNLSTLSDPVQLEVQVGWLLLQAPRWVFKE   120
CD16II_3     VDDSGEYRCQTNLSTLSDPVQLEVQVGWLLLQAPRWVFKE   120
             *.********************..*************

CD16I_1      EDPIHLRCHSWKNTALHKVTYLQNGKDRKYFHHNSDFHIP   160
CD16I_4      EDPIHLRCHSWKNTALHKVTYLQNGKDRKYFHHNSDFHIP   160
CD16I_3      EEPIHLRCHSWKNTALHKVTYLQNGKDRKYSHHNSDFHIP   160
CD16I_2      EDPIHLRCHSWKNTALHKVTYLQNGKDRKYFHHNSDFHIP   160
FCG3_HUMAN   EDPIHLRCHSWKNTALHKVTYLQNGKGRKYFHHNSDFYIP   160
CD16II_1     EDPIHLRCHSWKNTALHKVTYLQNGKGRKYFHHNSDFYIP   160
CD16II_4     EDPIHLRCHSWKNTALHKVTYLQNGKGRKYSHHNSDFYIP   160
CD16II_2     EDPIHLRCHSWKNTALHKVTYLQNGKDRKYFHHNSDFHIP   160
CD16II_3     EDPIHLRCHSWKNTALHKVTYLQNGKDRKYFHHNSDFHIP   160
             *.******************************  ******.**
```

FIG. 1B

```
CD16I_1      KATLKDSGSYFCRGLVGSKNVSSETVNITITQGLAVSTIS    200
CD16I_4      KATLKDSGSYFCRGLVGSKNVSSETVNITITQGLAVSTIS    200
CD16I_3      KATLKDSGSYFCRGLVGSKNVSSETVNITITQGLAVSTIS    200
CD16I_2      KATLKDSGSYFCRGLVGSKNVSSETVNITITQGLAVSTIS    200
FCG3_HUMAN   KATLKDSGSYFCRGLFGSKNVSSETVNITITQGLAVSTIS    200
CD16II_1     KATLKDSGPYFCRGLFGSKNVSSETVNTTITQGLAVSTIS    200
CD16II_4     KATLKDSGSYFCRGLFGSKNVSSETVNITITQGLAVSTIS    200
CD16II_2     KATLKDSGSYFCKGLVGSKNVSSETVNITIIQGLAVSTNS    200
CD16II_3     KATLKDSGSYFCRGLVGSKNVSSETVNITITQGLAVSTIS    200
             ******** *** **  **********.**.******* *

CD16I_1      SFSPPGYQVSFCLVMVLLFAVDTGLYFSVKTNI-------    233
CD16I_4      SFSPPGYQVSFCLVMVLLFAVDTGLYFSVKTNI-------    233
CD16I_3      SFSPPGYQVSFCLVMVLLFAVDTGLYFSVKTNI-------    233
CD16I_2      SFSPPGYQVSFCLVMVLLFAVDTGLYFSVKTNI-------    233
FCG3_HUMAN   SFFPPGYQVSFCLVMVLLFAVDTGLYFSVKTNIRSSTRDW    240
CD16II_1     SFFPPGYQVSFCLAMVLLFAVDTGLYFSVKTNIRSSTRDW    240
CD16II_4     SFFPPGYQVSFCLVMVLLFAVDTGLYFSVKTNIRSPTRDW    240
CD16II_2     SFFPPGYQVSFCLVMVLLFAVDTGLYFSVKTNIRSSTRDW    240
CD16II_3     SFFPPGYQVSFCLVMVLLFAVDTGLYFSVKTNIRSSTRDW    240
             ** *********.***************************

CD16I_1      ---------------                             233
CD16I_4      ---------------                             233
CD16I_3      ---------------                             233
CD16I_2      ---------------                             233
FCG3_HUMAN   KDHKFKWRKDPQDK                              254
CD16II_1     KDHKFKWRKDPQDK                              254
CD16II_4     KDHKFKWRKDPQDK                              254
CD16II_2     KDHKFKWRKDPQDK                              254
CD16II_3     KDHKFKWRKDPQDK                              254
```

Panel A: CD 16 Isoform-specific Oligonucleotide PC Primers:

```
         nt#    CD16p1              CD16P5 and CD16p6    nt#

Type I:  34  ATGTGGCAGCTGCTC........GAGCAGTGGCAGCAG      836
             ===============........==============
Type II: 34  ATGTGGCAGCTGCTC........GAGCAGTAGCAGCAG      836
```

Panel B: Restriction Digestion of CD 16 subtype with endonuclease DraI.

FIG. 3A

```
         1                                                                                              100
Four     ----------------------------------------------------------------------------------------------------
Three    ----------------------------------------------------------------------------------------------------
Two      ---------------------------------------------a------------------------------------------------------
Group1   ----------------------------------------------------------------------------------------------------
Wt       ATGTGGCAGCTGCTCCTCCCAACTGCTGCTCTGCTACTTCTAGTTTCAGCTGCATGGGACTGAAGATCTCCCAAAGGCTGTGGTGTTCCTGGAGCCTCAAT 101                                                                                            200
Four     -----------------------------------------------a-----------------------a--------------------------
Three    -----t-------------------------------------------------------------------a------------------------
Two      ---------------------------------------------a-----------------------a--------------------------
Group1   ----------------------------------------------------------------------------------------------------
Wt       GGTACAGGTGCTCGAGAAGGACAGTGTGACTCTGAAGTGCCAGGAGCCTACTCCCCTGAGGACAATTCCACACAGTGGTTTCACAATGAGAGCCTCAT 201                                                                                            300
Four     ----------------------------------------------------------------------------------------------------
Three    -------------------------------g------------------------------------------------------------t-------
Two      ----------------------------------------------------------------------------------------------------
Group1   ----------------------------------------------------------------------------------------------------
Wt       CTCAAGCCAGGCCTCGAGCTACTTCATTGACGCTGCCACAGTCGACGACAGTGGAGAGTACAGGTGCCAGACAAACCTCTCCACCCTCAGTGACCCGGTG 301                                                                                            400
Four     --------------ag------------------------------------------------------------------------------------
Three    --------------ag------------------------------------------------------------------------------------
Two      ----------------------------------------------------------------------------------------------------
Group1   ----------------------------------------------------------------------------------------------------
Wt       CAGCTAGAAGTCCATATCGGCTGGCTGTTGCTCCAGGCCCCCTCGGTGGGTGTTCAAGGAGGAAGACCCTATTCACCTGAGGTGTCACAGCTGGAAGAACA
```

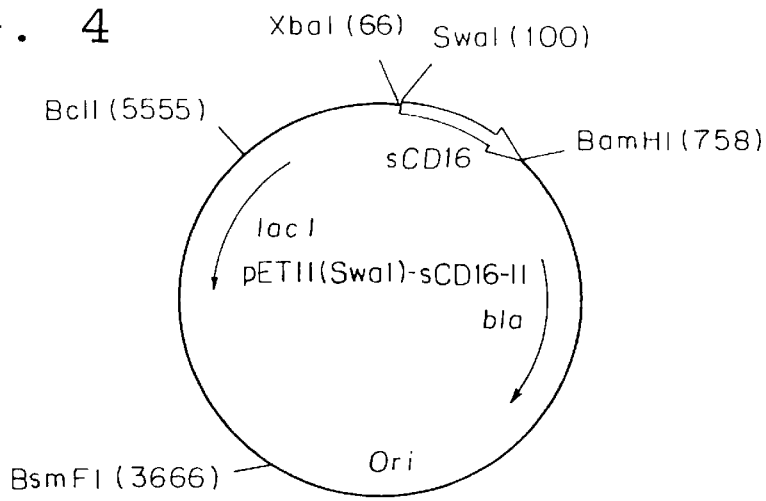

```
 10  ATG CGG ACT GAA GAT CTC CCA AAG GCT GTG GTG TTC CTG GAG CCT CAA TGG TAC AGG GTG
     TAC GCC TGA CTT CTA GAG GGT TTC CGA CAC CAC AAG GAC CTC GGA GTT ACC ATG TCC CAC
  1 ►Met Arg Thr Glu Asp Leu Pro Lys Ala Val Val Phe Leu Glu Pro Gln Trp Tyr Arg Val

70  CTC GAG AAG GAC AGT GTG ACT CTG AAG TGC CAG GGA GCC TAC TCC CCT GAG GAC AAT TCC
     GAG CTC TTC CTG TCA CAC TGA GAC TTC ACG GTC CCT CGG ATG AGG GGA CTC CTG TTA AGG
 21 ►Leu Glu Lys Asp Ser Val Thr Leu Lys Cys Gln Gly Ala Tyr Ser Pro Glu Asp Asn Ser

130  ACA CAG TGG TTT CAC AAT GAG AGC CTC ATC TCA AGC CAG GCC TCG AGC TAC TTC ATT GAC
     TGT GTC ACC AAA GTG TTA CTC TCG GAG TAG AGT TCG GTC CGG AGC TCG ATG AAG TAA CTG
 41 ►Thr Gln Trp Phe His Ans Glu Ser Leu Ile Ser Ser Gln Ala Ser Ser Tyr Phe Ile Asp

190  GCT GCC ACA GTC GAC GAC AGT GGA GAG TAC AGG TGC CAG ACA AAC CTC TCC ACC CTC AGT
     CGA CGG TGT CAG CTG CTG TCA CCT CTC ATG TCC ACG GTC TGT TTG GAG AGG TGG GAG TCA
 61 ►Ala Ala Thr Val Asp Asp Ser Gly Glu Tyr Arg Cys Gln Thr Asn Leu Ser Thr Leu Ser

250  GAC CCG GTG CAG CTA GAA GTC CAT ATC GGC TGG CTG TTG CTC CAG GCC CCT CGG TGG GTG
     CTG GGC CAC GTC GAT CTT CAG GTA TAG CCG ACC GAC AAC GAG GTC CGG GGA GCC ACC CAC
 81 ►Asp Pro Val Gln Leu Glu Val His Ile Gly Trp Leu Leu Leu Gln Ala Pro Arg Trp Val

310  TTC AAG GAG GAA GAC CCT ATT CAC CTG AGG TGT CAC AGC TGG AAG AAC ACT GCT CTG CAT
     AAG TTC CTC CTT CTG GGA TAA GTG GAC TCC ACA GTG TCG ACC TTC TTG TGA CGA GAC GTA
101 ►Phe Lys Glu Glu Asp Pro Ile His Leu Arg Cys His Ser Trp Lys Asn Thr Ala Leu His

370  AAG GTC ACA TAT TTA CAG AAT GGC AAA GGC AGG AAG TAT TTT CAT CAT AAT TCT GAC TTC
     TTC CAG TGT ATA AAT GTC TTA CCG TTT CCG TCC TTC ATA AAA GTA GTA TTA AGA CTG AAG
121 ►Lys Val Thr Tyr Leu Gln Asn Gly Lys Gly Arg Lys Tyr Phe His His Asn Ser Asp Phe

430  TAC ATT CCA AAA GCC ACA CTC AAA GAC AGC GGC TCC TAC TTC TGC AGG GGG CTT TTT GGG
     ATG TAA GGT TTT CGG TGT GAG TTT CTG TCG CCG AGG ATG AAG ACG TCC CCC GAA AAA CCC
141►Tyr Ile Pro Lys Ala Thr Leu Lys Asp Ser Gly Ser Tyr Phe Cys Arg Gly Leu Phe Gly

490  AGT AAA AAT GTG TCT TCA GAG ACT GTG AAC ATC ACC ATC ACT CAA GGT TTG GCA GTG TCA
     TCA TTT TTA CAC AGA AGT CTC TGA CAC TTG TAG TGG TAG TGA GTT CCA AAC CGT CAC AGT
161 ►Ser Lys Asn Val Ser Ser Glu Thr Val Asn Ile Thr Ile Thr Gln Gly Leu Ala Val Ser

550  ACC ATC TCA TCA TTC TTT CCA CCT GGG TAC CAA GTC TCT TTC TGC TTG GTG ATG GTA CTC
     TGG TAG AGT AGT AAG AAA GGT GGA CCC ATG GTT CAG AGA AAG ACG AAC CAC TAC CAT GAG
181 ►Thr Ile Ser Ser Phe Phe Pro Pro Gly Tyr Gln Val Ser Phe Cys Leu Val Met Val Leu

610  CTT TTT GCA GTG GAC ACA GGA CTA TAT TTC TCT GTG AAG ACA AAC TAA
     GAA AAA CGT CAC CTG TGT CCT GAT ATA AAG AGA CAC TTC TGT TTG ATT
201 ►Leu Phe Ala Val Asp Thr Gly Leu Tyr Phe Ser Val Lys Thr Asn ...
```

FIG. 5

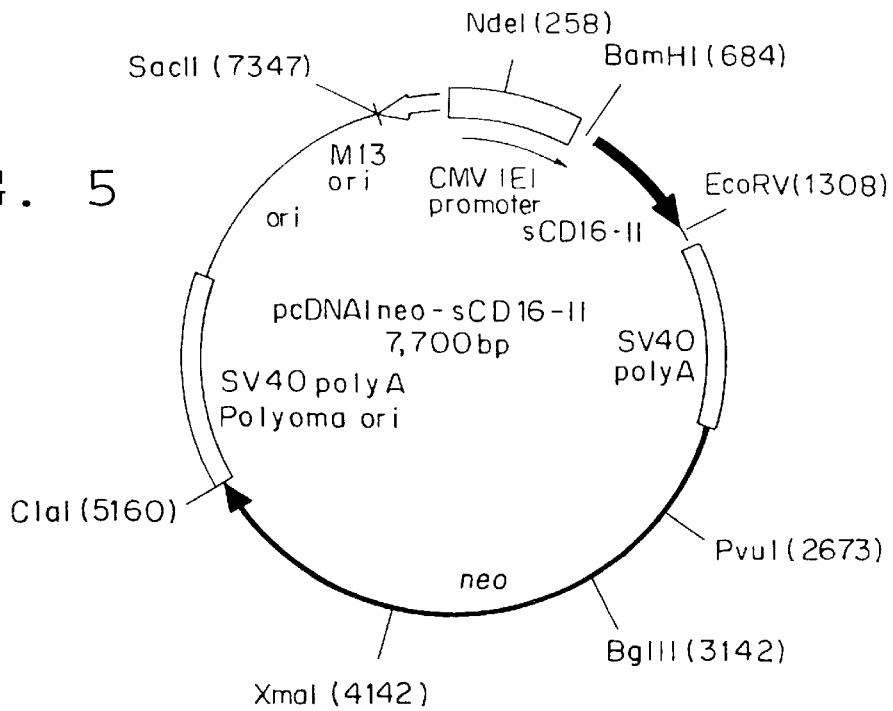

```
     BamHI
  1  GGATCC ATG TGG CAG CTG CTC CTC CCA ACT GCT CTG CTA CTT CTA GTT TCA
         1► Met Trp Gln Leu Leu Leu Pro Thr Ala Leu Leu Leu Leu Val Ser

52  GCT GGC ATG CGG ACT GAA GAT CTC CCA AAG GCT GTG GTG TTC CTG GAG CCT
 16  ►Ala Gly Met Arg Thr Glu Asp Leu Pro Lys Ala Val Val Phe Leu Glu Pro

103  CAA TGG TAC AGG GTG CTC GAG AAG GAC AGT GTG ACT CTG AAG TGC CAG GGA
 33  ►Gln Trp Tyr Arg Val Leu Glu Lys Asp Ser Val Thr Leu Lys Cys Gln Gly

154  GTC TAC TCC CCT GAG GAC AAT TCC ACA CAG TGG TTT CAC AAT GAG AGC CTC
 50  ►Ala Tyr Ser Pro Glu Asp Asn Ser Thr Gln Trp Phe His Asn Glu Ser Leu

205  ATC TCA AGC CAG GCC TCG AGC TAC TTC ATT GAC GCT GCC ACA GTC GAC GAC
 67  ►Ile Ser Ser Gln Ala Ser Ser Tyr Phe Ile Asp Ala Ala Thr Val Asp Asp

256  AGT GGA GAG TAC AGG TGC CAG ACA AAC CTC TCC ACC CTC AGT GAC CCG GTG
 84  ►Ser Gly Glu Tyr Arg Cys Gln Thr Asn Leu Ser Thr Leu Ser Asp Pro Val

307  CAG CTA GAA GTC CAT ATC GGC TGG CTG TTG CTC CAG GCC CCT CGG TGG GTG
101  ►Gln Leu Glu Val His Ile Gly Trp Leu Leu Leu Gln Ala Pro Arg Trp Val

358  TTC AAG GAG GAA GAC CCT ATT CAC CTG AGG TGT CAC AGC TGG AAG AAC ACT
118  ►Phe Lys Glu Glu Asp Pro Ile His Leu Arg Cys His Ser Trp Lys Asn Thr

409  GCT CTG CAT AAG GTC ACA TAT TTA CAG AAT GGC AAA GGC AGG AAG TAT TTT
135  ►Ala Leu His Lys Val Thr Tyr Leu Gln Asn Gly Lys Gly Arg Lys Tyr Phe

460  CAT CAT AAT TCT GAC TTC TAC ATT CCA AAA GCC ACA CTC AAA GAC AGC GGC
152  ►His His Asn Ser Asp Phe Tyr Ile Pro Lys Ala Thr Leu Lys Asp Ser Gly

511  TCC TAC TTC TGC AGG GGG CTT TTT GGG AGT AAA AAT GTG TCT TCA GAG ACT
169  ►Ser Tyr Phe Cys Arg Gly Leu Phe Gly Ser Lys Asn Val Ser Ser Glu Thr

562  GTG AAC ATC ACC ATC ACT CAA GGT TTG GCA GTG TCA ACC ATC TCA TCA TTC
186  ►Val Asn Ile Thr Ile Thr Gln Gly Leu Ala Val Ser Thr Ile Ser Ser Phe
                            EcoRV
613  TTT TGA GAATTCGATATC
203  ►Phe ...
```

CD16-II VARIANTS

CROSS REFERENCE TO RELATED APPLICATIONS

The present application is a division of copending parent application Ser. No. 08/433,123 filed May 3, 1995.

FIELD OF INVENTION

The present invention relates to human CD16-II protein variants, DNA sequences coding for them, their use in therapy and/or in diagnosis of autoimmune diseases and inflammatory illnesses, as well as pharmaceutical compositions comprising them.

BACKGROUND OF THE INVENTION

CD16, also called Fcγ receptor-III (FcγR-III), is a low affinity receptor for Immunoglobulin G (IgG). With other receptors of the immunoglobulin Fc portion (FcγR-I, FcγR-II, FcεR-I), CD16 plays an important role in mediating autoimmunity and inflamm atory responses.

Studies using monoclonal antibodies against CD16 have established this receptor's role in removing immune complexes from circulation and in mediating antibody-dependent cell mediated cellular cytotoxicity (ADCC) (see for example Van de Winkel et al., *Immunol. Today*, 14, 1993, pp.215–221). The binding of IgG with CD16 elicits NK/LGL cell activation and triggers ADCC. ADCC can be halted in the presence of high levels of soluble CD16.

It has been found (see Mathiot et al., *J. Clin. Immunol.*, 13, (1), 1993, pp. 41–8) that the level of soluble CD16 was significantly decreased in patients with multiple myeloma compared with healthy volunteers. In addition a stage-dependent decrease of soluble CD16 was observed, with a highly significant difference between stage I and stages II+III myeloma patients. Therefore the measurement of soluble CD16 in serum is both a diagnostic and a prognostic marker of myeloma, which can be useful to define and guide novel immunomodulatory therapies of the disease.

It has further been found that CD16 is present in human serum and other body fluids and is elevated at sites of inflammation (see Fleit et al., *Blood*, 79, (10), 1992, pp. 2721–8).

From Ravetch et al. (*J. Exp. Med.*, 170, 1989, pp. 481–97) it is clear that there are at least two isoforms of human CD16, type 1 and type 2, that can be designated as CD16-I and CD16-II, respectively. These two isoforms of CD16 are encoded by two separate but related genes, NA1 and NA2.

From Scallon et al. (*PNAS USA*, 86, pp.5079–83, July 1989) it is evident that CD16-I and CD16-II are distinct in both structure and cellular expression. CD16-I is expressed predominantly on the surface of neutrophils and monocytes, whereas CD16-II is expressed predominantly on the surface of macrophages, natural killer cells and large granular lymphocytes (NK/LGL). Furthermore, these two types of CD-16 are associated with the cell surface via two distinct mechanisms: CD16 type I is associated with the cell surface by glycosyl-phosphotidylinositol (GPI) linkage; whereas CD16 type II is anchored on the membrane with about 20 extra amino acids. Furthermore, the N-terminus of the mature CD16 has been investigated and the methionine residue at position 18 was identified as the N-terminal residue of the mature protein. Thus, the initial translation product contains a 17-amino acid signal peptide. The transmembrane region of CD16-II is shown to be from amino acid 209 to 229, whereas CD16-I is reported lacking transmembranal and cytoplasmic domains.

It has been determined that a single amino acid at position 203, Ser, found in isoform I versus Phe, found in type II, determines the membrane anchoring mechanism (see Lanier et al., *Science*, 246, 1989, pp. 1611–3).

For human CD16-I, a polymorphism has been reported previously, as is evident from FIG. 1, whereas only one alternative nucleic acid sequence encoding CD16-II has been published until now (Ravetch et al., *J. Exp. Med.*, 170, 1989, pp. 481–97).

Recently, Huizinga et al. (see *Blood*, 76, pp. 1927–, 1990) published evidence that CD16-I deficiency is related to neonatal isoimmune neutropenia.

Bredius et al. (in *Immunology*, 83, pp. 624–, 1994) reported specifically that CD16-I-NA1 exhibited a 21–25% higher IgG1 mediated phagocytosis than CD16-I-NA2.

It has been reported that circulating levels of soluble CD16 are reduced in Multiple Myeloma, and an inhibitory effect of sCD16 on myeloma cells and pokeweed mitogen (PWM) -induced B-cell proliferation have been reported (see, respectively, Hoover et al., *J. Cli. Inve.*, 95(1), pp.241–7, 1995) and Teillaud et al., *Blood*, 82(10), Nov. 15 1993).

European Patent Application EP 343 950 generally discloses soluble and membrane-bound human FcγR-III polypeptides as well as nucleic acids capable of encoding the same. In particular, the sequence of a CD16-I variant and the sequence of CD16-II are shown in the Figures. This patent application further discloses various utilities for these polypeptides.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is based on the discovery of new human CD16-II variant clones. They have been isolated by using an RT-PCR (Reverse Transcriptase-Polymerase Chain Reaction) -based strategy using designed isoform-specific oligonucleotide primers. In particular, from a pooled human lung RNA extract, CD16-II has been amplified via RT-PCR. These CD16-II variants provide a therapeutic intervening approach and/or a diagnostic tool for autoimmune and inflammatory diseases. As they are natural variants of the CD16-II sequence previously published, the polypeptides of the present invention can be used for any of the utilities previously disclosed for CD16-II. All of the utilities for CD16-II made evident from any of the publications disclosed herein are hereby incorporated herein by reference, and particularly those in European application 343,950.

The main object of the present invention are the polypeptides comprising respectively the SEQ ID NO: 1, 2, 3 and 4.

Another object of the invention are the DNA molecules comprising the DNA sequences coding for each of the four polypeptides, as shown in FIG. 3, including nucleotide sequences substantially the same. "Nucleotide sequences substantially the same" includes all other nucleic acid sequences which, by virtue of the degeneracy of the genetic code, also code for the given amino acid sequences. Preparation of an alternative nucleotide sequence encoding the same polypeptide but differing from the natural sequence due to changes permitted by the known degeneracy of the genetic code, can be achieved by site-specific mutagenesis of DNA that encodes an earlier prepared variant or a nonvariant version of the polypeptide of the present invention. Site-specific mutagenesis allows the production of variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., DNA, 2:183 (1983), the disclosure of which is incorporated herein by reference. As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, editor, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.*, 153:3 (1987)) may be employed to obtain single-stranded DNA. In general, site-directed mutagenesis in accordance herewith is performed by first obtaining a single-stranded vector that includes within its sequence a DNA sequence that encodes the relevant protein. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

As already stated, the proteins of the invention are useful in the therapy and/or diagnosis of autoimmune diseases and inflammatory illnesses. Therefore, in a further aspect, the present invention provides the use of each protein of the invention in the manufacture of a medicament for the treatment of autoimmune diseases and inflammatory illnesses.

The medicament is preferably presented in the form of a pharmaceutical composition comprising one of the proteins of the invention together with one or more pharmaceutically acceptable carriers and/or excipients. Such pharmaceutical compositions form yet a further aspect of the present invention.

The invention will now be described by means of the following Example, which should not be construed as in any way limiting the present invention. The Example will refer to the Figures specified here below.

BRIEF DESCRIPTION OF THE DRAWINGS

FIG. 1 shows the sequence alignment of various CD16 variants, including those of the present invention. The alignment has been done by using the PC/Gene Software. The symbol "*" shows that a position in the alignment is "perfectly conserved". The symbol "." shows that a position is "well conserved". A blank space shows that a position is not conserved. "CD16I_1" is the human CD16-I aa sequence reported in Simmons et al., *Nature*, 333, pp. 568–570, 1988 (SEQ ID NO:5). "CD16I_2" is the human CD16-I aa sequence reported in Peltz et al., *PNAS USA*, 86, pp. 1013–7, 1989 (SEQ ID NO:6). "CD16I_3" is the human CD16-I aa sequence reported in Scallon et al., *PNAS USA*, 86, pp. 5079–83, 1989 (SEQ ID NO:7). "CD16I_4" is the human CD16-I aa sequence reported in Lanier, *Science*, 246, pp. 1611–3, 1989 (SEQ ID NO:8). "FCG3 human" is the CD16-II aa sequence reported in Ravetch et al., *J. Exp. Med.*, 170, pp. 481–7, 1989 (SEQ ID NO:9). "CD16II_1", "CD16II_2", "CD16II_3" and "CD16II_4" are the CD16-II aa sequences of the proteins of the present invention respectively SEQ ID NO: 1, 2, 3 and 4.

Figure 3B:
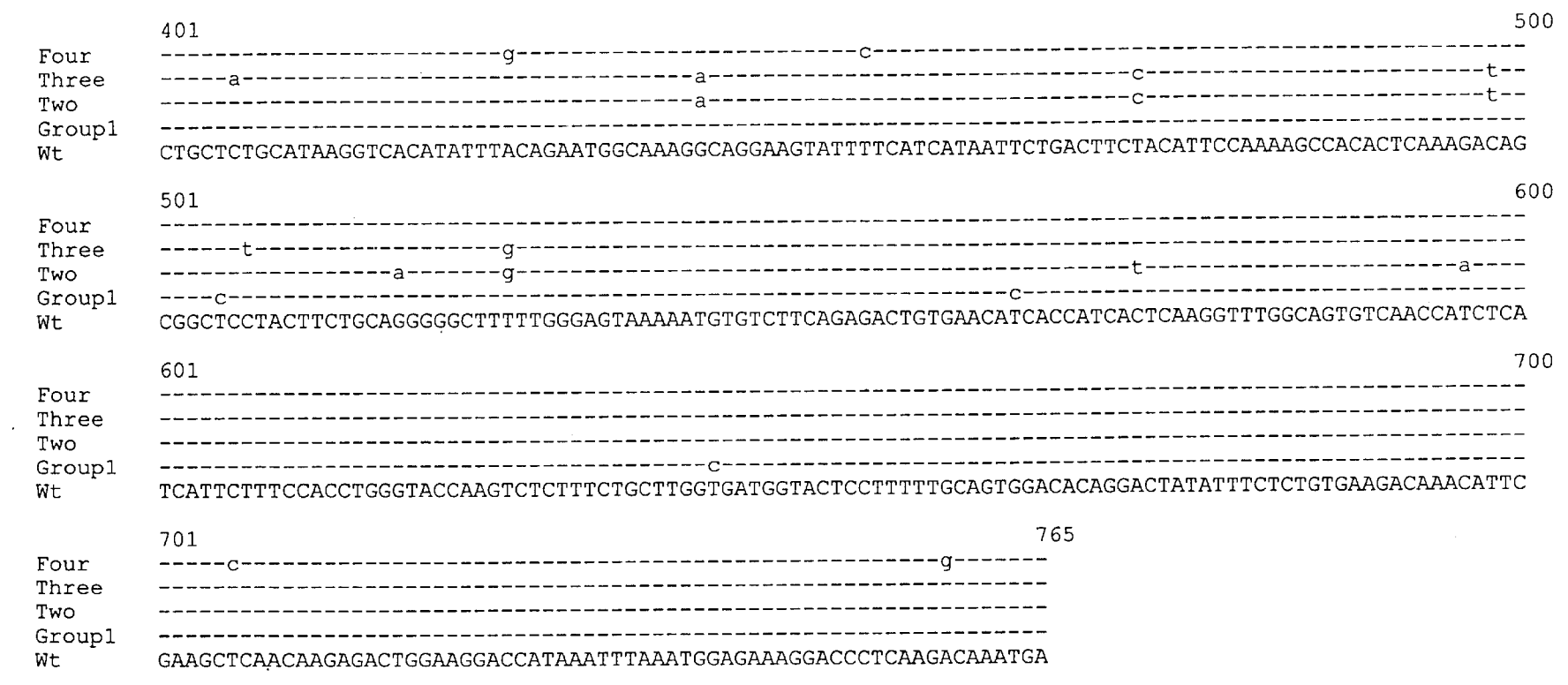

FIG. 3 is a comparison of the CD16-II variants of the invention in nucleic acid sequence. The first four sequences (SEQ ID NO: 12, 13, 14, and 15, respectively) are those coding for the four variants of the present invention, whereas the last is that already known and reported in Ravetch et al., *J. Exp. Med.*, 170, pp. 481–7, 1989 (SEQ ID NO:16). Conserved nucleotides are indicated by dashed lines, whereas changed ones are spelled in lower case alphabet.

FIG. 4 shows the restriction map of plasmid pcDNAI/neo-sCD16-II, useful as expression vector for CD16-II variants in CHO cells, as well as the nucleotide and amino acid sequences of the coding portion thereof (SEQ ID NOS: 17 and 18).

FIG. 5 shows the restriction map of plasmid pET11 (SwaI)-CD16-II, useful as expression vector for CD16-II variants in *E. coli* as well as the nucleotide and amino acid sequences of the coding portion thereof (SEQ ID NOS: 19 and 20).

EXAMPLE

Enzymes and Reagents

Figure 2:
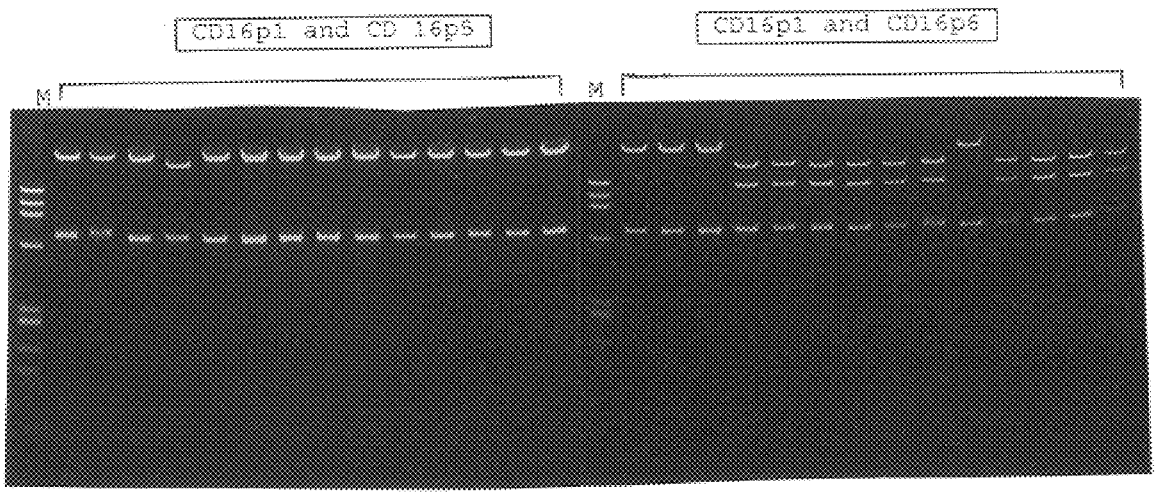
FIG. 2 A–B illustrates the reverse transcriptase based polymerase chain reaction (RT-PCR) amplification of human CD16. Panel A shows the isoform-specific oligonucleotide PCR primers. The primers on the line marked "Type I" (CD16p1 (nucleotides 7–21 of SEQ ID NO:17) and CD16p5 (SEQ ID NO:11)) were designed from the published human CD16-I sequence. The primers on the line marked "Type II" (CD16p1 (nucleotides 7–21 of SEQ ID NO:17) and CD16p6 (SEQ ID NO:12)) were designed from the human CD16-II sequence. CD16 isoform specific oligonucleotide primers for the 3' end are shown as a single mismatch at position 829, G to A. The melting temperature ($T_m$) of 3' PCR primers CD16-I and CD16-II are 53.9 and 46.30° C., respectively. Panel B shows the result of restriction analysis of CD16 clones carried out using Endonuclease DraI. The banding pattern for CD16-I and CD16-II are visualised; shown on the left panel are type I clones from PCR amplification using primer pair CD16p1 and CD16p5, whereas the right panel shows type II clones from PCR amplification using primer pair CD16p1 and CD16p6.

Human lung polyA$^+$RNA was purchased from Clontech. Moloney Murine Leukaemia Virus RNase H$^-$Reverse transcriptase (M-MLV H$^-$RT) was purchased from BRL Life Technologies, Inc. Vent™ DNA polymerase, restriction endonucleases, and modifying enzymes were obtained from New England Biolabs. Sequenase Version 2.0 was purchased form US Biochemicals. The plasmid used for subcloning, pBluescript+SK, was purchased from Stratagene and used according to the manufacturer's recommendations.

Oligonucleotide Primer Design

To amplify CD16 type I and type II, isoform-specific oligonucleotide primers were designed as follows: 1) CD16p1: ATGTGGCAGCTGCTC (nucleotides 7–21 of SEQ ID NO:17) as 5' PCR primer for both type I and type II; 2) CD16p5 and CD16p6: CTGCTGCCACTGCTC (SEQ ID NO:21) and CTGCTGCTACTGCTC (SEQ ID NO:22) as 3' PCR primers for type I and type II, respectively. These primers were designed to amplify each isoform of CD16 specifically under a given annealing temperature, i.e., 53.9° C. for type I whereas 46.3° C. for type-II (FIG. 2).

Synthesis of cDNA and PCR Amplification

RNA prepared from human lung tissue was used as a template for first strand cDNA synthesis. A 50 µl reaction mixture was set up containing 2µ Poly-A+RNA, 2.5 µg oligo -dT primer, 500 mM dNTPs, 50 mM Tris-HCl, pH 8.8, 75 mM KCl, 10 mM Dithiothreitol, 3 mM $MgCl_2$, and 100 units M-MLV H RT. To stop the reaction, 5 ml of 500 ml mM EDTA was added to the mixture. The resultant mixture was extracted with an equal volume of Phenol/Chloroform/IAA (25:24:1) and precipitated with 3 volume of ethanol. The precipitated reaction was resuspended in 10 µl of TE, and 1 ml was used for PCR amplification. PCR amplifications were performed in 100 ml reaction mixture containing 200 µM of dATP, dCTP, dGTP, dTTP, 10 mM KCl, 20 mM Tris-HCl, pH 8.8, 10 mm $(NH_4)_2SO_4$, 2 mM $MgSO_4$, 0.1% Triton X-100, 1 µl of µl (above) cDNA, and 4 units of Vent™. Thermocycles were programmed as follows: 99° C., 10-minute incubation followed by 25 cycles of 94° C., 45 seconds; 54° C. for type I or 46° C. for type II, 1 minute; and 75° C., 1 minute, using GeneAmp PCR System 9600 (Perkin Elmer). After agarose gel electrophoresis, resulting PCR products were extracted with phenol/chloroform, precipitated with ethanol, and digested with BamHI to yield compatible restriction ends for subcloning into pBluescript+SK or further characterization.

Characterization of CD16-II Clones

Cloning and sequencing of the PCR products were carried out following the standard molecular protocol (according to Sambrook et al., *Molecular Cloning—A Laboratory Manual*, Cold Spring Harbor Laboratory Press, 1989). Sequence data was analyzed using UWGCG (version 7.3) nucleic acid analysis programs following the standard protocol.

RT-PCR Amplification of CD16

Using the isoform-specific PCR primers, CD16-I and -II were amplified specifically using RT-PCR. The sequence comparison of CD16-I and CD16-II shows they are 98% identical. To amplify CD16-I, isoform-specific oligonucleotide primers were designed and used to direct PCR amplifications under specific conditions, using the cDNA generated from human lung tissue mRNA. The isoform-specific oligonucleotide primers for type I and II were chosen from the 3'-untranslated region of the genes, nucleotides 822 to 836, where a single mismatch was found at nucleotide 829 (G for type-I whereas A for type-II, see FIG. 2, Panel A). Fourteen clones, picked randomly, were identified to be type I and type II by an endonuclease DraI digestion (FIG. 2, Panel B).

It was the high sequence-identity of CD16-I and -II that led to the cloning strategy of using isoform-specific oligonucleotide primers for specific isoform isolation. Due to a 98% identity in nucleotide sequence between CD16-I and CD16-II, isoform-specific oligonucleotide primers 15(mers) were designed and used to direct PCR amplifications under specific conditions (primer-template annealing temperature 54° C. and 46° C. for type-I and type-II, respectively). These annealing condition can stabilise the perfect match of CD16p5 to type I cDNA template at 54° C., and that of CD16p6 to type II cDNA template at a lower annealing condition, 46° C. Taking advantage of a single mismatch at nucleotide #829, according to the original cDNA numbering (Ravetch et al., *J. Exp. Med.*, 170, 1989, pp.481–7), 7 nucleotides upstream and 7 nucleotides downstream including the central nucleotide #829 (G for type-I and A for type-II), a total of 15 nucleotides were included in designing 15 mers PCR primers to maintain specificity for subtype-I or -II (see FIG. 2, Panel A). As a result, subtype-I and subtype-II were isolated as shown in Panel B (FIG. 2, Panel B) and later on analyzed.

Sequence Analysis of CD16-II Clones

In addition to polymorphic variants of CD16-I, a similar type of sequence variation was found in CD16-II (see FIG. 3 for nucleic acid and FIG. 1 for amino acid sequences). Full length nucleotide sequence analyses were carried out and confirmed that cDNA clones for type-I contain a stop codon at 234 whereas those for type-II bear a codon for Arg at 234 and a stop codon at 255. In FIG. 3, twenty-five nucleotide changes were observed. Of the 25 mismatches, 17 were found to cause codon changes (see FIG. 3 and FIG. 1). The remaining 8 were fond to be silent mutations. Of the changes, 21 were from adenine or thymine to cytosine or guanine. Four of twenty-five changes were thymine to adenine. The deduced amino acid sequence revealed that most variations found in type-I also occurred in type-II (7 of 17, see FIG. 1). In addition, 10 other variations throughout the type-II translated region were observed. However, nine residues in the extracellular domain of the receptor critical for IgG binding (according to Hibbs et al., *J. of Immunology*, 152, 1994, pp. 4466–74), Trp131, Gln-Asn-Gly-Lys 143–146 (residues 143–146 of SEQ ID NOS:6–9), Arg-Lys-Tyr 148–150, and Gly168, remain unchanged. Interestingly, glycine at position 147 located between two important motifs Gln-Asn-Gly-Lys 143–146 (residues 143–146 of SEQ ID NOS:6–9) and Arg-Lys-Tyr 148–150, was found changed to an aspartic acid, a conserved change. Apparently, glycine 147 can be mutated to, at least, alanine without severely altering the IgG binding property. Lastly, in one of the four variants of CD16-II there was a mutation observed in the putative transmembrane domain, Val214 to Ala, a conserved change. However, a motif Leu-Phe-Ala-Val-Asp-Thr-Gly-Leu (residues 218–225 of SEQ ID NOS:6–9) in the transmembrane domain was found identical to the previously reported sequence. And this amino acid motif was found completely conserved through human and mouse CD16 and human, mouse, and rat FcεRIa.

Genetic Engineering of CD16-II Variants for Expression in CHO Cells and *E. coli*

The following procedures are applicable for the expression and purification of each of the CD16-II variants of the invention, even though CD16-II, generically, will be mentioned.

In order to engineer soluble CD16-II (sCD16-II) for CHO expression, oligonucleotide primer CD16p14 is designed as GGGAATTCAAAAGAATGATGAGATGGT (SEQ ID NO:23). CD16p14 is designed so that a TGA stop codon is inserted after the Phe codon (Phe#203 is characteristic for CD16-II). CD16p1 and CD16p14 were used to amplify the soluble form of CD16-II (see FIG. 4). The exact C terminus of the naturally occurring soluble form in CD16-II is yet to be determined; however, by choosing this truncation the engineered form of soluble CD16-II will contain the extracellular portion of the molecule.

For *E. coli* expression of sCD16-II, oligonucleotide primers, CD16-(SwaI) and CD16N233, are designed as TTTGGATCCAAGCTTAGTTTGTCTTCA-CAGAGAAATAGAGACCT (SEQ ID NO:24) and TTTATTTAAATGCGTACTGAAGATCTCCCAAAG (SEQ ID NO:25), respectively.

CD16-(SwaI) and CD16N233 primers are designed so that in *E. coli*, amino acid sequence from #18 to #233 (see FIG. 5) could be produced, which is the mature protein, also containing the transmembranal domain.

Methotrexate (MTX) amplification is used in CHO cell expression of CD16-II.

Large scale DNA preparation of plasmid pcDNAI/neo-sCD16-II (see FIG. 4) is carried out using Qiagen column followed by ethanol precipitation and was used for stable transfection by cotransfecting with Dα vector (containing the DHFR gene) for MTX selection. CHO transfectants are pooled and fully amplified to 5 μM MTX. In order to produce sCD16 for purification, the highest sCD16 producing pool is selected and cultured in MTX-free basal medium (JRH, Biosciences) or MTX-free low protein medium (SFM-II, Gibco). The culture medium is collected at 24, 48 or 72 hours and used for purification on IgG affinity chromatography. Analysis of sCD16-II is done using $OD_{280}$, SDS-PAGE, ELISA, Western blotting, amino acid composition analysis and N-terminal sequencing.

For *E. coli* expression of sCD16-II, isopropylthio-β-galactoside (IPTG) induced BL21/DE3 cells are incubated in lysis buffer and the soluble material analyzed using SDS-PAGE and Western blotting with polyclonal anti-hCD16 antisera.

Soluble CD16-II expressed in *E. coli*, is also confirmed using N-terminal sequencing.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within references cited herein are also entirely incorporated by reference.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

I claim:

1. An isolated DNA molecule comprising a DNA sequence encoding the polypeptide of SEQ ID NO:1.

2. The isolated DNA molecule in accordance with claim 1, wherein said DNA sequence is nucleotides 1–762 of SEQ ID NO:15.

3. An isolated DNA molecule comprising a DNA sequence encoding the polypeptide of SEQ ID NO:2.

4. The isolated DNA molecule in accordance with claim 3, wherein said DNA sequence is nucleotides 1–762 of SEQ ID NO:14.

5. An isolated DNA molecule comprising a DNA sequence encoding the polypeptide of SEQ ID NO:3.

6. The isolated DNA molecule in accordance with claim 5, wherein said DNA sequence is nucleotides 1–762 of SEQ ID NO:13.

7. An isolated DNA molecule comprising a DNA sequence encoding the polypeptide of SEQ ID NO:4.

8. The isolated DNA molecule in accordance with claim 7, wherein said DNA sequence is nucleotides 1–762 of SEQ ID NO:12.

* * * * *

UNITED STATES PATENT AND TRADEMARK OFFICE
CERTIFICATE OF CORRECTION

PATENT NO. : 5,998,166

DATED : December 7, 1999

INVENTOR(S) : Shun Luo

It is certified that error appears in the above-identified patent and that said Letters Patent is hereby corrected as shown below:

Column 3, line 66, change "FIG. 1" to --FIGS. 1A-1B--.

Column 4, line 40, change "FIG. 3" to --FIGS. 3A-3B--.

Column 6, lines 25 and 26, change "FIG. 3" to --FIGS. 3A-3B--.

Column 6, line 26, change "FIG. 1" to --FIGS. 1A-1B--.

Column 6, line 32, change "(see FIG. 3 and FIG. 1)" to --(see FIGS. 3A-3B and FIGS. 1A-1B)--.

Column 6, line 30, change "FIG. 3" to --FIGS. 3A-3B--.

Column 6, line 38, change "FIG. 1" to --FIGS. 1A-1B--.

Signed and Sealed this

Twenty-ninth Day of August, 2000

Attest:

Q. TODD DICKINSON

*Attesting Officer*     *Director of Patents and Trademarks*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

```
Ser Asp Pro Val Gln Leu Glu Val His Ile Gly Trp Leu Leu Leu Gln
            100                 105                 110
Ala Pro Arg Trp Val Phe Lys Glu Glu Asp Pro Ile His Leu Arg Cys
            115                 120                 125
His Ser Trp Lys Asn Thr Ala Leu His Lys Val Thr Tyr Leu Gln Asn
        130                 135                 140
Gly Lys Gly Arg Lys Tyr Phe His His Asn Ser Asp Phe Tyr Ile Pro
145                 150                 155                 160
Lys Ala Thr Leu Lys Asp Ser Gly Pro Tyr Phe Cys Arg Gly Leu Phe
                165                 170                 175
Gly Ser Lys Asn Val Ser Ser Glu Thr Val Asn Thr Thr Ile Thr Gln
                180                 185                 190
Gly Leu Ala Val Ser Thr Ile Ser Ser Phe Phe Pro Pro Gly Tyr Gln
            195                 200                 205
Val Ser Phe Cys Leu Ala Met Val Leu Leu Phe Ala Val Asp Thr Gly
        210                 215                 220
Leu Tyr Phe Ser Val Lys Thr Asn Ile Arg Ser Ser Thr Arg Asp Trp
225                 230                 235                 240
Lys Asp His Lys Phe Lys Trp Arg Lys Asp Pro Gln Asp Lys
                245                 250
```

(2) INFORMATION FOR SEQ ID NO:2:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Trp Gln Leu Leu Leu Pro Thr Ala Leu Leu Leu Leu Val Ser Ala
1               5                   10                  15
Gly Met Arg Thr Glu Asp Leu Pro Lys Ala Val Val Phe Leu Glu Pro
            20                  25                  30
Gln Trp Tyr Ser Val Leu Glu Lys Asp Ser Val Thr Leu Lys Cys Gln
            35                  40                  45
Gly Ala Tyr Ser Pro Glu Asp Asn Ser Thr Gln Trp Phe His Lys Glu
50                  55                  60
Asn Leu Ile Ser Ser Gln Ala Ser Ser Tyr Phe Ile Asp Ala Ala Thr
65                  70                  75                  80
Val Asp Asp Ser Gly Glu Tyr Arg Cys Gln Thr Asn Leu Ser Thr Leu
                85                  90                  95
Ser Asp Pro Val Gln Leu Glu Val Gln Val Gly Trp Leu Leu Leu Gln
            100                 105                 110
Ala Pro Arg Trp Val Phe Lys Glu Glu Asp Pro Ile His Leu Arg Cys
            115                 120                 125
His Ser Trp Lys Asn Thr Ala Leu His Lys Val Thr Tyr Leu Gln Asn
        130                 135                 140
Gly Lys Asp Arg Lys Tyr Phe His His Asn Ser Asp Phe His Ile Pro
145                 150                 155                 160
Lys Ala Thr Leu Lys Asp Ser Gly Ser Tyr Phe Cys Lys Gly Leu Val
                165                 170                 175
Gly Ser Lys Asn Val Ser Ser Glu Thr Val Asn Ile Thr Ile Ile Gln
                180                 185                 190
Gly Leu Ala Val Ser Thr Asn Ser Ser Phe Phe Pro Pro Gly Tyr Gln
```

```
                    195                 200                 205
Val Ser Phe Cys Leu Val Met Val Leu Leu Phe Ala Val Asp Thr Gly
    210                 215                 220
Leu Tyr Phe Ser Val Lys Thr Asn Ile Arg Ser Ser Thr Arg Asp Trp
225                 230                 235                 240
Lys Asp His Lys Phe Lys Trp Arg Lys Asp Pro Gln Asp Lys
                245                 250

(2) INFORMATION FOR SEQ ID NO:3:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Trp Gln Leu Leu Pro Thr Ala Leu Leu Leu Val Ser Ala
1               5                   10                  15
Gly Met Arg Thr Glu Asp Leu Pro Lys Ala Val Val Phe Leu Glu Pro
                20                  25                  30
Gln Trp Tyr Arg Val Leu Glu Lys Asp Ser Val Thr Leu Lys Cys Gln
            35                  40                  45
Gly Ala Tyr Ser Pro Glu Asp Asn Ser Thr Gln Trp Phe His Lys Glu
        50                  55                  60
Asn Leu Ile Ser Ser Gln Ala Ser Ser Tyr Phe Ile Asp Ala Ala Thr
65                  70                  75                  80
Val Asp Asp Ser Gly Glu Tyr Arg Cys Gln Thr Asn Leu Ser Thr Leu
                85                  90                  95
Ser Asp Pro Val Gln Leu Glu Val Gln Val Gly Trp Leu Leu Leu Gln
                100                 105                 110
Ala Pro Arg Trp Val Phe Lys Glu Glu Asp Pro Ile His Leu Arg Cys
            115                 120                 125
His Ser Trp Lys Asn Thr Ala Leu His Lys Val Thr Tyr Leu Gln Asn
        130                 135                 140
Gly Lys Asp Arg Lys Tyr Phe His His Asn Ser Asp Phe His Ile Pro
145                 150                 155                 160
Lys Ala Thr Leu Lys Asp Ser Gly Ser Tyr Phe Cys Arg Gly Leu Val
                165                 170                 175
Gly Ser Lys Asn Val Ser Ser Glu Thr Val Asn Ile Thr Ile Thr Gln
                180                 185                 190
Gly Leu Ala Val Ser Thr Ile Ser Ser Phe Phe Pro Pro Gly Tyr Gln
            195                 200                 205
Val Ser Phe Cys Leu Val Met Val Leu Leu Phe Ala Val Asp Thr Gly
        210                 215                 220
Leu Tyr Phe Ser Val Lys Thr Asn Ile Arg Ser Ser Thr Arg Asp Trp
225                 230                 235                 240
Lys Asp His Lys Phe Lys Trp Arg Lys Asp Pro Gln Asp Lys
                245                 250

(2) INFORMATION FOR SEQ ID NO:4:

(i) SEQUENCE CHARACTERISTICS:
        (A) LENGTH: 254 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:4:

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
130                 135                 140

Gly Lys Gly Arg Lys Tyr Ser His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Pro Thr Arg Asp Trp
225                 230                 235                 240

Lys Asp His Lys Phe Lys Trp Arg Lys Asp Pro Gln Gly Lys
                245                 250
```

(2) INFORMATION FOR SEQ ID NO:5:

(i) SEQUENCE CHARACTERISTICS:
       (A) LENGTH: 233 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:5:

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80
```

```
Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
                195                 200                 205

Val Ser Phe Cys Leu Val Met Val Leu Leu Phe Ala Val Asp Thr Gly
                210                 215                 220

Leu Tyr Phe Ser Val Lys Thr Asn Ile
225                 230
```

(2) INFORMATION FOR SEQ ID NO:6:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Asn Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Val Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190
```

```
Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

(2) INFORMATION FOR SEQ ID NO:7:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Trp Gln Leu Leu Pro Thr Ala Leu Leu Leu Val Ser Ala
1               5                   10                  15

Gly Met Arg Thr Glu Asp Leu Pro Lys Ala Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Glu Pro Ile His Leu Arg Cys
            115                 120                 125

His Ser Trp Lys Asn Thr Ala Leu His Lys Val Thr Tyr Leu Gln Asn
        130                 135                 140

Gly Lys Asp Arg Lys Tyr Ser His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230
```

(2) INFORMATION FOR SEQ ID NO:8:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                      55                  60

Ser Leu Ile Ser Ser Gln Ala Ser Ser Tyr Phe Ile Asp Ala Ala Thr
65                      70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Asp Arg Lys Tyr Phe His His Asn Ser Asp Phe His Ile Pro
145                     150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230

(2) INFORMATION FOR SEQ ID NO:9:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                      55                  60

Ser Leu Ile Ser Ser Gln Ala Ser Ser Tyr Phe Ile Asp Ala Ala Thr
65                      70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
```

```
                115             120                 125
His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GAGCAGTGGC AGCAG                                               15

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GAGCAGTAGC AGCAG                                               15

(2) INFORMATION FOR SEQ ID NO:12:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
ATGTGGCAGC TGCTCCTCCC AACTGCTCTG CTACTTCTAG TTTCAGCTGG CATGCGGACT      60

GAAGATCTCC CAAAGGCTGT GGTGTTCCTG GAGCCTCAAT GGTACAGGGT GCTCGAGAAG     120

GACAGTGTGA CTCTGAAGTG CCAGGGAGCC TACTCCCCTG AGGACAATTC CACACAGTGG    180

TTTCACAATG AGAGCCTCAT CTCAAGCCAG GCCTCGAGCT ACTTCATTGA CGCTGCCACA    240

GTCGACGACA GTGGAGAGTA CAGGTGCCAG ACAAACCTCT CCACCCTCAG TGACCCGGTG    300

CAGCTAGAAG TCCATATCGG CTGGCTGTTG CTCCAGGCCC CTCGGTGGGT GTTCAAGGAG    360
```

```
GAAGACCCTA TTCACCTGAG GTGTCACAGC TGGAAGAACA CTGCTCTGCA TAAGGTCACA      420

TATTTGCAGA ATGGCAAAGG CAGGAAGTAT TCTCATCATA ATTCTGACTT CTACATTCCA      480

AAAGCCACAC TCAAAGACAG CGGCTCCTAC TTCTGCAGGG GGCTTTTTGG GAGTAAAAAT      540

GTGTCTTCAG AGACTGTGAA CATCACCATC ACTCAAGGTT TGGCAGTGTC AACCATCTCA      600

TCATTCTTTC CACCTGGGTA CCAAGTCTCT TTCTGCTTGG TGATGGTACT CCTTTTTGCA      660

GTGGACACAG GACTATATTT CTCTGTGAAG ACAAACATTC GAAGCCCAAC AAGAGACTGG      720

AAGGACCATA AATTTAAATG GAGAAAGGAC CCTCAAGGCA AATGA                      765

(2) INFORMATION FOR SEQ ID NO:13:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATGTGGCAGC TGCTCCTCCC AACTGCTCTG CTACTTCTAG TTTCAGCTGG CATGAGGACT       60

GAAGATCTCC CAAAGGCTGT GGTGTTCCTG GAGCCTCAAT GGTACAGGGT GCTCGAGAAG      120

GACAGTGTGA CTCTGAAGTG CCAGGGAGCC TACTCCCCTG AGGACAATTC CACACAGTGG      180

TTTCACAAAG AGAACCTCAT CTCAAGCCAG GCCTCGAGCT ACTTCATTGA CGCTGCCACA      240

GTCGACGACA GTGGAGAGTA CAGGTGCCAG ACGAACCTCT CCACCCTCAG TGACCCGGTG      300

CAGCTAGAAG TCCAAGTCGG CTGGCTGTTG CTCCAGGCCC CTCGGTGGGT GTTCAAGGAG      360

GAAGACCCTA TTCACCTGAG GTGTCACAGC TGGAAGAACA CTGCTATGCA TAAGGTCACA      420

TATTTACAGA ATGGCAAAGA CAGGAAGTAT TTTCATCATA ATTCTGACTT CCACATTCCA      480

AAAGCCACAC TCAAAGATAG CGGCTCTTAC TTCTGCAGGG GGCTTGTTGG GAGTAAAAAT      540

GTGTCTTCAG AGACTGTGAA CATCACCATC ACTCAAGGTT TGGCAGTGTC AACCATCTCA      600

TCATTCTTTC CACCTGGGTA CCAAGTCTCT TTCTGCTTGG TGATGGTACT CCTTTTTGCA      660

GTGGACACAG GACTATATTT CTCTGTGAAG ACAAACATTC GAAGCTCAAC AAGAGACTGG      720

AAGGACCATA AATTTAAATG GAGAAAGGAC CCTCAAGACA AATGA                      765

(2) INFORMATION FOR SEQ ID NO:14:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATGTGGCAGC TGCTCCTCCC AACTGCTCTG CTACTTCTAG TTTCAGCTGG CATGCGGACT       60

GAAGATCTCC CAAAGGCTGT GGTGTTCCTG GAGCCTCAAT GGTACAGTGT GCTCGAGAAG      120

GACAGTGTGA CTCTGAAGTG CCAGGGAGCC TACTCCCCTG AGGACAATTC CACACAATGG      180

TTTCACAAAG AGAACCTCAT CTCAAGCCAG GCCTCGAGCT ACTTCATTGA CGCTGCCACA      240

GTCGACGACA GTGGAGAGTA CAGGTGCCAG ACAAACCTCT CCACCCTCAG TGACCCGGTG      300

CAGCTAGAAG TCCAAGTCGG CTGGCTGTTG CTCCAGGCCC CTCGGTGGGT GTTCAAGGAG      360

GAAGACCCTA TTCACCTGAG GTGTCACAGC TGGAAGAACA CTGCTCTGCA TAAGGTCACA      420
```

TATTTACAGA ATGGCAAAGA CAGGAAGTAT TTTCATCATA ATTCTGACTT CCACATTCCA    480

AAAGCCACAC TCAAAGATAG CGGCTCCTAC TTCTGCAAGG GGCTTGTTGG GAGTAAAAAT    540

GTGTCTTCAG AGACTGTGAA CATCACCATC ATTCAAGGTT TGGCAGTGTC AACCAACTCA    600

TCATTCTTTC CACCTGGGTA CCAAGTCTCT TTCTGCTTGG TGATGGTACT CCTTTTTGCA    660

GTGGACACAG GACTATATTT CTCTGTGAAG ACAAACATTC GAAGCTCAAC AAGAGACTGG    720

AAGGACCATA AATTTAAATG GAGAAAGGAC CCTCAAGACA AATGA    765

(2) INFORMATION FOR SEQ ID NO:15:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATGTGGCAGC TGCTCCTCCC AACTGCTCTG CTACTTCTAG TTTCAGCTGG CATGCGGACT    60

GAAGATCTCC CAAAGGCTGT GGTGTTCCTG GAGCCTCAAT GGTACAGGGT GCTCGAGAAG    120

GACAGTGTGA CTCTGAAGTG CCAGGGAGCC TACTCCCCTG AGGACAATTC CACACAGTGG    180

TTTCACAATG AGAGCCTCAT CTCAAGCCAG GCCTCGAGCT ACTTCATTGA CGCTGCCACA    240

GTCGACGACA GTGGAGAGTA CAGGTGCCAG ACAAACCTCT CTACCCTCAG TGACCCGGTG    300

CAGCTAGAAG TCCATATCGG CTGGCTGTTG CTCCAGGCCC CTCGGTGGGT GTTCAAGGAG    360

GAAGACCCTA TTCACCTGAG GTGTCACAGC TGGAAGAACA CTGCTCTGCA TAAGGTCACA    420

TATTTACAGA ATGGCAAAGG CAGGAAGTAT TTTCATCATA ATTCTGACTT CTACATTCCA    480

AAAGCCACAC TCAAAGACAG CGGCCCCTAC TTCTGCAGGG GGCTTTTTGG GAGTAAAAAT    540

GTGTCTTCAG AGACTGTGAA CACCACCATC ACTCAAGGTT TGGCAGTGTC AACCATCTCA    600

TCATTCTTTC CACCTGGGTA CCAAGTCTCT TTCTGCTTGG CGATGGTACT CCTTTTTGCA    660

GTGGACACAG GACTATATTT CTCTGTGAAG ACAAACATTC GAAGCTCAAC AAGAGACTGG    720

AAGGACCATA AATTTAAATG GAGAAAGGAC CCTCAAGACA AATGA    765

(2) INFORMATION FOR SEQ ID NO:16:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

ATGTGGCAGC TGCTCCTCCC AACTGCTCTG CTACTTCTAG TTTCAGCTGG CATGCGGACT    60

GAAGATCTCC CAAAGGCTGT GGTGTTCCTG GAGCCTCAAT GGTACAGGGT GCTCGAGAAG    120

GACAGTGTGA CTCTGAAGTG CCAGGGAGCC TACTCCCCTG AGGACAATTC CACACAGTGG    180

TTTCACAATG AGAGCCTCAT CTCAAGCCAG GCCTCGAGCT ACTTCATTGA CGCTGCCACA    240

GTCGACGACA GTGGAGAGTA CAGGTGCCAG ACAAACCTCT CCACCCTCAG TGACCCGGTG    300

CAGCTAGAAG TCCATATCGG CTGGCTGTTG CTCCAGGCCC CTCGGTGGGT GTTCAAGGAG    360

GAAGACCCTA TTCACCTGAG GTGTCACAGC TGGAAGAACA CTGCTCTGCA TAAGGTCACA    420

TATTTACAGA ATGGCAAAGG CAGGAAGTAT TTTCATCATA ATTCTGACTT CTACATTCCA    480

```
AAAGCCACAC TCAAAGACAG CGGCTCCTAC TTCTGCAGGG GGCTTTTTGG GAGTAAAAAT        540

GTGTCTTCAG AGACTGTGAA CATCACCATC ACTCAAGGTT TGGCAGTGTC AACCATCTCA        600

TCATTCTTTC CACCTGGGTA CCAAGTCTCT TTCTGCTTGG TGATGGTACT CCTTTTTGCA        660

GTGGACACAG GACTATATTT CTCTGTGAAG ACAAACATTC GAAGCTCAAC AAGAGACTGG        720

AAGGACCATA AATTTAAATG GAGAAAGGAC CCTCAAGACA AATGA                       765

(2) INFORMATION FOR SEQ ID NO:17:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..645

(xi) SEQUENCE DESCRIPTION: SEQ ID NO:17:

ATG CGG ACT GAA GAT CTC CCA AAG GCT GTG GTG TTC CTG GAG CCT CAA          48
Met Arg Thr Glu Asp Leu Pro Lys Ala Val Val Phe Leu Glu Pro Gln
 1               5                  10                  15

TGG TAC AGG GTG CTC GAG AAG GAC AGT GTG ACT CTG AAG TGC CAG GGA         96
Trp Tyr Arg Val Leu Glu Lys Asp Ser Val Thr Leu Lys Cys Gln Gly
            20                  25                  30

GCC TAC TCC CCT GAG GAC AAT TCC ACA CAG TGG TTT CAC AAT GAG AGC        144
Ala Tyr Ser Pro Glu Asp Asn Ser Thr Gln Trp Phe His Asn Glu Ser
        35                  40                  45

CTC ATC TCA AGC CAG GCC TCG AGC TAC TTC ATT GAC GCT GCC ACA GTC        192
Leu Ile Ser Ser Gln Ala Ser Ser Tyr Phe Ile Asp Ala Ala Thr Val
    50                  55                  60

GAC GAC AGT GGA GAG TAC AGG TGC CAG ACA AAC CTC TCC ACC CTC AGT        240
Asp Asp Ser Gly Glu Tyr Arg Cys Gln Thr Asn Leu Ser Thr Leu Ser
65                  70                  75                  80

GAC CCG GTG CAG CTA GAA GTC CAT ATC GGC TGG CTG TTG CTC CAG GCC        288
Asp Pro Val Gln Leu Glu Val His Ile Gly Trp Leu Leu Leu Gln Ala
                85                  90                  95

CCT CGG TGG GTG TTC AAG GAG GAA GAC CCT ATT CAC CTG AGG TGT CAC        336
Pro Arg Trp Val Phe Lys Glu Glu Asp Pro Ile His Leu Arg Cys His
            100                 105                 110

AGC TGG AAG AAC ACT GCT CTG CAT AAG GTC ACA TAT TTA CAG AAT GGC        384
Ser Trp Lys Asn Thr Ala Leu His Lys Val Thr Tyr Leu Gln Asn Gly
        115                 120                 125

AAA GGC AGG AAG TAT TTT CAT CAT AAT TCT GAC TTC TAC ATT CCA AAA        432
Lys Gly Arg Lys Tyr Phe His His Asn Ser Asp Phe Tyr Ile Pro Lys
    130                 135                 140

GCC ACA CTC AAA GAC AGC GGC TCC TAC TTC TGC AGG GGG CTT TTT GGG        480
Ala Thr Leu Lys Asp Ser Gly Ser Tyr Phe Cys Arg Gly Leu Phe Gly
145                 150                 155                 160

AGT AAA AAT GTG TCT TCA GAG ACT GTG AAC ATC ACC ATC ACT CAA GGT        528
Ser Lys Asn Val Ser Ser Glu Thr Val Asn Ile Thr Ile Thr Gln Gly
                165                 170                 175

TTG GCA GTG TCA ACC ATC TCA TCA TTC TTT CCA CCT GGG TAC CAA GTC        576
Leu Ala Val Ser Thr Ile Ser Ser Phe Phe Pro Pro Gly Tyr Gln Val
            180                 185                 190

TCT TTC TGC TTG GTG ATG GTA CTC CTT TTT GCA GTG GAC ACA GGA CTA        624
Ser Phe Cys Leu Val Met Val Leu Leu Phe Ala Val Asp Thr Gly Leu
        195                 200                 205
```

| | | |
|---|---|---|
| TAT TTC TCT GTG AAG ACA AAC TAA | | 648 |
| Tyr Phe Ser Val Lys Thr Asn | | |
| 210 215 | | |

(2) INFORMATION FOR SEQ ID NO:18:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:18:

```
Met Arg Thr Glu Asp Leu Pro Lys Ala Val Val Phe Leu Glu Pro Gln
  1               5                  10                  15

Trp Tyr Arg Val Leu Glu Lys Asp Ser Val Thr Leu Lys Cys Gln Gly
             20                  25                  30

Ala Tyr Ser Pro Glu Asp Asn Ser Thr Gln Trp Phe His Asn Glu Ser
         35                  40                  45

Leu Ile Ser Ser Gln Ala Ser Ser Tyr Phe Ile Asp Ala Ala Thr Val
     50                  55                  60

Asp Asp Ser Gly Glu Tyr Arg Cys Gln Thr Asn Leu Ser Thr Leu Ser
 65                  70                  75                  80

Asp Pro Val Gln Leu Glu Val His Ile Gly Trp Leu Leu Leu Gln Ala
                 85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
        115                 120                 125

Lys Gly Arg Lys Tyr Phe His His Asn Ser Asp Phe Tyr Ile Pro Lys
    130                 135                 140

Ala Thr Leu Lys Asp Ser Gly Ser Tyr Phe Cys Arg Gly Leu Phe Gly
145                 150                 155                 160

Ser Lys Asn Val Ser Ser Glu Thr Val Asn Ile Thr Ile Thr Gln Gly
                165                 170                 175

Leu Ala Val Ser Thr Ile Ser Ser Phe Phe Pro Pro Gly Tyr Gln Val
            180                 185                 190

Ser Phe Cys Leu Val Met Val Leu Leu Phe Ala Val Asp Thr Gly Leu
        195                 200                 205

Tyr Phe Ser Val Lys Thr Asn
    210                 215
```

(2) INFORMATION FOR SEQ ID NO:19:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 7..615

(xi) SEQUENCE DESCRIPTION: SEQ ID NO:19:

| | | |
|---|---|---|
| GGATCC ATG TGG CAG CTG CTC CTC CCA ACT GCT CTG CTA CTT CTA GTT | | 48 |
|        Met Trp Gln Leu Leu Leu Pro Thr Ala Leu Leu Leu Leu Val | | |
|                         220                225 | | |
| TCA GCT GGC ATG CGG ACT GAA GAT CTC CCA AAG GCT GTG GTG TTC CTG | | 96 |

```
Ser Ala Gly Met Arg Thr Glu Asp Leu Pro Lys Ala Val Val Phe Leu
230                 235                 240                 245

GAG CCT CAA TGG TAC AGG GTG CTC GAG AAG GAC AGT GTG ACT CTG AAG      144
Glu Pro Gln Trp Tyr Arg Val Leu Glu Lys Asp Ser Val Thr Leu Lys
                250                 255                 260

TGC CAG GGA GCC TAC TCC CCT GAG GAC AAT TCC ACA CAG TGG TTT CAC      192
Cys Gln Gly Ala Tyr Ser Pro Glu Asp Asn Ser Thr Gln Trp Phe His
            265                 270                 275

AAT GAG AGC CTC ATC TCA AGC CAG GCC TCG AGC TAC TTC ATT GAC GCT      240
Asn Glu Ser Leu Ile Ser Ser Gln Ala Ser Ser Tyr Phe Ile Asp Ala
        280                 285                 290

GCC ACA GTC GAC GAC AGT GGA GAG TAC AGG TGC CAG ACA AAC CTC TCC      288
Ala Thr Val Asp Asp Ser Gly Glu Tyr Arg Cys Gln Thr Asn Leu Ser
    295                 300                 305

ACC CTC AGT GAC CCG GTG CAG CTA GAA GTC CAT ATC GGC TGG CTG TTG      336
Thr Leu Ser Asp Pro Val Gln Leu Glu Val His Ile Gly Trp Leu Leu
310                 315                 320                 325

CTC CAG GCC CCT CGG TGG GTG TTC AAG GAG GAA GAC CCT ATT CAC CTG      384
Leu Gln Ala Pro Arg Trp Val Phe Lys Glu Glu Asp Pro Ile His Leu
                330                 335                 340

AGG TGT CAC AGC TGG AAG AAC ACT GCT CTG CAT AAG GTC ACA TAT TTA      432
Arg Cys His Ser Trp Lys Asn Thr Ala Leu His Lys Val Thr Tyr Leu
            345                 350                 355

CAG AAT GGC AAA GGC AGG AAG TAT TTT CAT CAT AAT TCT GAC TTC TAC      480
Gln Asn Gly Lys Gly Arg Lys Tyr Phe His His Asn Ser Asp Phe Tyr
        360                 365                 370

ATT CCA AAA GCC ACA CTC AAA GAC AGC GGC TCC TAC TTC TGC AGG GGG      528
Ile Pro Lys Ala Thr Leu Lys Asp Ser Gly Ser Tyr Phe Cys Arg Gly
    375                 380                 385

CTT TTT GGG AGT AAA AAT GTG TCT TCA GAG ACT GTG AAC ATC ACC ATC      576
Leu Phe Gly Ser Lys Asn Val Ser Ser Glu Thr Val Asn Ile Thr Ile
390                 395                 400                 405

ACT CAA GGT TTG GCA GTG TCA ACC ATC TCA TCA TTC TTT TGAGAATTCG      625
Thr Gln Gly Leu Ala Val Ser Thr Ile Ser Ser Phe Phe
                410                 415

ATATC                                                                630

(2) INFORMATION FOR SEQ ID NO:20:

(i) SEQUENCE CHARACTERISTICS:
        (A) LENGTH: 203 amino acids
        (B) TYPE: amino acid
        (D) TOPOLOGY: linear (ii) MOLECULE TYPE: protein (xi) SEQUENCE DESCRIPTION: SEQ ID NO:20:

Met Trp Gln Leu Leu Leu Pro Thr Ala Leu Leu Leu Leu Val Ser Ala
 1               5                  10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
```

```
                100                 105                 110
Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe
                195                 200
```

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CTGCTGCCAC TGCTC                                              15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CTGCTGCTAC TGCTC                                              15

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GGGAATTCAA AAGAATGATG AGATGGT                            27

(2) INFORMATION FOR SEQ ID NO:24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TTTGGATCCA AGCTTAGTTT GTCTTCACAG AGAAATAGAG ACCT            44

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TTTATTTAAA TGCGTACTGA AGATCTCCCA AAG    33